United States Patent [19]

Hu et al.

[11] 4,404,278
[45] Sep. 13, 1983

[54] METHODS AND COMPOSITIONS FOR ASSAYING FOR THE PRODUCTION OF 1,4-DIHYDROPYRIDYL

[75] Inventors: Mae W. Hu, Sunnyvale; Floyd W. Colvin, Redwood City; Edwin F. Ullman, Atherton, all of Calif.

[73] Assignee: Syva Company, Palo Alto, Calif.

[21] Appl. No.: 209,365

[22] Filed: Nov. 24, 1980

[51] Int. Cl.$^3$ .................. G01N 33/54; C12N 9/96
[52] U.S. Cl. .......................... 435/7; 435/188; 435/810; 436/518; 436/537; 436/547; 436/808
[58] Field of Search .................. 435/7, 188, 810; 23/230 B; 424/1, 85, 8, 12; 260/112, 121; 436/518, 537, 547, 808

[56] References Cited

U.S. PATENT DOCUMENTS

| | | | |
|---|---|---|---|
| 4,067,774 | 1/1978 | Rubenstein | 435/7 |
| 4,134,792 | 1/1979 | Boguslaski et al. | 435/7 |
| 4,233,402 | 11/1980 | Maggio et al. | 435/7 |
| 4,238,565 | 12/1980 | Hornby et al. | 435/7 |
| 4,252,783 | 2/1981 | Kam et al. | 424/8 |
| 4,318,707 | 3/1982 | Litman et al. | 435/7 |
| 4,341,866 | 7/1982 | Yoshida et al. | 435/7 |

OTHER PUBLICATIONS

Parker, *Radioimmunoassay of Biologically Active Compounds*, Prentice-Hall, Inc., Englewood Cliffs, (1976), pp.36–67.
Kanemitsu, "Antibodies to Coenzymes", *Chem. Absts.*, vol. 93, No. 24 (1980), pp. 315–316, Absts. No. 225617s.
Bredehorst, "Determination of radioimmunoassay of the Sum of Oxidized and reduced forms of NAD and NADP in picomole quantities from the same Acid Extract" *Chem. Absts.* vol. 91, No. 21 (1979) pp. 274–275.
Ogievetskaya et al., "Study of the Localization of Adenine Components in Chicken Myofibers by the Ferritin Antibody Method" *Chem. Absts.*, vol. 90, No. 17, (1979), pp. 295–296, Absts. No. 135336t.
Schrader et al., "Radioimmunoassay for Adenosine in Biological Samples", *Chem. Absts.* vol 90, No. 11, (1979) p. 264, Absts. No. 83207e.
Bredehorst et al., "Production of Antibodies Against ADP-Ribose and 5'-AMP with aid of $N^6$-Carboxy Methylated ADP-Ribose Conjugates", *Chem. Absts.*, vol. 88, No. 13 (1978), p. 199, Absts. No. 85510f.

*Primary Examiner*—Thomas G. Wiseman
*Attorney, Agent, or Firm*—Bertram I. Rowland

[57] ABSTRACT

Methods and compositions for assaying for coenzymes having N-substituted 1,4-dihydropyridyl as the active portion of the prosthetic group. The conversion of NAD to NADH is widely measured both for determining NAD-NADH (including the analogs thereof) dependent enzymes and enzymes that can be coupled to NAD-NADH dependent enzymes, and for determining ligands or receptors in competitive protein binding assays. Antibodies specific for NADH in the presence of NAD are employed, providing enhanced fluorescence over the normal fluorescence of unbound NADH. By determining the rate of formation of NADH or the concentration of NADH, the analyte or enzyme of interest can be determined.

6 Claims, No Drawings

METHODS AND COMPOSITIONS FOR ASSAYING FOR THE PRODUCTION OF 1,4-DIHYDROPYRIDYL

BACKGROUND OF THE INVENTION

1. Field of the Invention

In many assays, there is an interest in determining the amount of rate of change in the concentration of NADH. A large number of enzymes of interest use NAD or NADP or the reduced forms as coenzymes. The rate of formation of the reduced form can be followed by the fluorescence of the reduced form. However, in most situations, a significant amount of endogenous fluorescence is present at the wavelength of the NADH emission. In view of the low quantum yield of fluorescence of NADH, small concentrations of the reduced coenzyme is quantiated by fluorescence spectroscopy only marginally more effectively than by adsorption spectroscopy.

It is therefore desirable to find ways to enhance the signal obtained from the NADH. Desirably, the ways should be simple and not subject to interference, particularly in view of the relatively large amounts of NAD derivatives which will usually be encountered in the assay medium.

2. Description of the Prior Art

Holbrook and Wolfe, Biocheminstry (1972), 41, 2499, describes fluorescent studies of NADH bound to malate dehydrogenase. Torikata et al., J. Biol. Chem. 254, 3516–3520 (1979) describes NAD quenching of tryptophan fluorescence in malate dehydrogenase. Baici et al., Eur. J. Biochem., 83, 601–607 (1978) describes the fluorescent properties of sNADH and its complex with octopine dehydrogenase. U.K. Pat. No. 1,532,694 teaches using NADH fluorescence in enzyme assays.

SUMMARY OF THE INVENTION

Methods and compositions are used in determining the amount of coenzymes having a 1,4-dihydropyridyl active group, such as reduced NAD, its phosphate or other analogs by measuring the fluorescence of the 1,4-dihydropyridyl enhanced by binding to a specific receptor, which distinguishes the reduced form from the oxidized form, N-substituted pyridyl. Particularly, antibodies are made which recognize the reduced form of the dihydropyridyl resulting in substantial enhancements in fluorescence. Further enhancement can be achieved by labeling the antibodies with fluorescent compounds emitting in the absorption band of the dihydropyridyl. The enhancement of the fluorescence can be used for determining the presence and/or concentration of NAD dependent enzymes, substances which can be coupled in one or more reactions resulting in the conversion of NAD to NADH or their analogs, and analytes in competitive protein binding assays employing NAD dependent enzymes as a label or coupling reagent.

DESCRIPTION OF THE SPECIFIC EMBODIMENTS

Methods are provided for assays involving formation of coenzymes having a 1,4-dihydropyridyl active group, such as the reduced forms of NAD, NADP, or other analogs thereof, e.g. 3-thionicotinamide adenine dinucleotide (sNADH). Hereafter NAD and NADH will be used as paradigmatic or coenzymes having 1,4-dihydropyridyl functionalities as their prosthetic group.

The methods normally involve an assay for an NAD dependent enzyme, an assay for an analyte, either ligand or receptor, involving an enzyme label, where the enzyme is NAD dependent or the product from the enzyme can be coupled with the transformation of NAD to NADH, either enzymatically catalyzed or non-enzymatically catalyzed.

In performing the assay method, the usual protocols are employed where NAD is transformed to NADH, but in the subject invention, antibodies are added which can distinguish between NADH and NAD (in effect, between an N-substituted pyridyl and the 1,4-dihydro derivative particularly the 3-formamide). The antibodies recognize the reduced form in the presence of the oxidized form. Sufficient antibody is added to bind to a substantial proportion of the NADH which will be formed under the conditions of the assay, usually sufficient to bind at least about 20%, preferably at least in about stoichiometric amounts, more preferably in substantial excess. The amount of the 1,4-dihydropyridyl that is formed is measured by illuminating the assay medium with a wavelength of light usually at or about the absorption maximum for the particular 1,4-dihydropyridyl compound, and following the emission of light at or near the wavelength of the emission maximum. These wavelengths will be 340 nm and 440 nm, respectively, for NADH but may differ with other derivatives.

To further enhance the quantum yield, the antibodies may be conjugated with compounds which fluoresce at wavelengths that the dihydropyridyl absorbs, but fluoresce weakly or not at all at wavelengths which are emitted by the particular dihydropyridyl derivative. Various fluorescent compounds can be employed. A preferred class has 1 to 2 fused aromatic rings of 5 to 6 annular members, carbocyclic or heterocyclic having C, N, S and O as annular members, such as indoles, e.g. tryptophan, naphthalenes, quinolines, benzofurans, and oxazoles.

These energy transfer compounds for the most part will emit light in the range of about 320 to 400 nm. A sufficient number of the energy transfer compounds will be bound to the antibody to provide for a high likelihood of excitation transfer between the exciting molecule and the NADH bound by the antibody. Usually, there will be at least 2 and more, usually 5 to 10 or more of the energy transfer compound covalently conjugated to IgG antibody; with IgM antibody as much as fivefold higher; and with Fab fragments, usually about 1 to 8. The total number will be based upon the efficiency of transfer to the bound NADH, and for intact IgG antibodies will usually not exceed about 20.

Enzymes which can be assayed more effectively by following the production of NADH by the enhanced fluorescence of the subject invention will for the most part be oxidoreductases, particularly under the I.U.B. classification 1.1.1, 1.2.1, 1.3.1, 1.4.1, 1.5.1, 1.6.1, 1.8.1 and 1.41.1 or enzymes which produce, either directly or indirectly, substrates for oxidoreductases. Of particular interest are the dehydrogenases, particularly dehydrogenases oxidizing alcohols to oxo or non-oxo-carbonyl groups, or amino to oxo or the like. Individual enzymes include alcohol dehydrogenase, 1.1.1.1; diaphorase, 1.6.4.3; glutamate dehydrogenase, 1.4.1.3; lactate dehydrogenase, 1.1.1.27; malate dehydrogenase, 1.1.1.37; glucose-6-phosphate dehydrogenase 1.1.1.49, and the like. For each of the NAD dependent enzymes, assays have been reported in the literature in which the formation of NADH is followed. In accordance with the subject invention, sufficient amount of the antiNADH is added to provide for substantial enhancement of the NADH fluorescence, when the assay sample is illuminated with light usually at or about the NADH absorption maximum. In view of the substantial enhancements obtained with the antiNADH, smaller concentrations can be measured or shorter times can be employed while maintaining the same degree of sensitivity.

Where an assay for an analyte is involved, a wide variety of assays employ enzymes as labels. One method is described in U.S. Pat. No. 3,817,837, which involves an enzyme-ligand conjugate, where binding of a receptor for the ligand results in reduction in activity of the enzyme. The portion describing the method appears in Columns. 3-6 and is incorporated herein by reference. Another method is described in U.S. Pat. No. Re. 29,169 which employs an enzyme-ligand label but involves separation of enzyme-ligand conjugate bound to receptor and unbound enzyme-ligand conjugate. Another method may be found in copending application Ser. No. 751,504, which involves an enzyme substrate-analyte conjugate, where the substrate may or may not be NAD. The appropriate portions of these references describing the methods are incorporated herein by reference.

For the most part, the assays will share some common attributes. The pH will normally be from about 5 to 11. Aqueous solutions will be employed, normally having less than about 40% of an inert organic solvent, usually less than about 20%. For the most part, the organic solvents will be oxygenated organic solvents, e.g. ethers, alcohols, and amides. Temperatures will normally range from about 0° to 60° C., usually from about 20° to 40° C. Concentrations of analytes and their specific receptors will generally be from about $10^{-4}$ to $10^{-18}M$, usually about $10^{-8}$–$10^{-14}M$, while concentrations of the pyridyl moiety will be about $10^{-1}$ $10^{-10}$, usually about $10^{-1}$ to $10^{-8}M$. Various buffers can be employed, such as phosphate, borate, tris, carbonate, bicine, and the like. Times for the assay will vary widely depending on the nature and sensitivity of the assay.

The immunogen employed for preparation of the antibodies will require only the nicotinamide portion of NADH. Either the reduced form of nicotinamide, either alkylated or glycosylated, particularly with a 5-carbon sugar, may be employed or a compound simulating the conformation of the reduced form of the nicotinamide may be employed. Where the adenine portion of the NADH is present in the immunogen, antibodies to this portion of the molecule must be prevented from forming or removed. Formation of antiadenine antibodies may be avoided by inducing immune tolerance in the animals or employing monoclonal antibody techniques. Unwanted antibodies can be removed by immunoadsorption techiques.

It is found that the reduced form of nicotinamide when conjugated to an antigen as an immunogen apparently does not produce satisfactory antisera in sheep. Therefore, other techniques are preferably employed when using the reduced form as part of the immunogen, such as in vitro sensitization of lymphocytes and fusion with a myeloma fusogen to produce hybridomas capable of producing monoclonal antibodies having the desired specificity. A single cell suspension of spleen cells is prepared, viable cells are isolated and seated in nutrient medium containing fetal calf serum and the immunogen added to a concentration not exceeding about 1%. Non-adherent cells are isolated and the buffy-coat obtained from Ficoll-Hypaque gradient centrifugation isolated and used for fusion in accordance with conventional techniques.

More conveniently, the reduced form of the nicotinamide may be simulated employing a meta-substituted benzamide.

For the most part, these compounds will have the following formula:

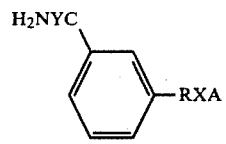

wherein:

R is a linking group, normally having only carbon, hydrogen and oxygen, wherein oxygen is oxy, either hydroxy or ether, R may be aliphatic or heterocyclic, saturated or unsaturated, when heterocyclic having only a single oxygen atom as an annular heteroatom; R may have from 1 to 6, usually 2 to 5 carbon atoms, and from 0 to 5, usually 0 to 4 oxygen atoms as oxy-hydroxy or ether;

X is a bond, methylene group, or oxygen containing functionality capable of forming a stable bond to an amino or hydroxyl group, particularly acyl groups, such as non-oxocarbonyl, sulfonyl, phosphoryl, and the like, particularly organic and inorganic acid groups;

Y is chalcogen: oxygen or sulfur;

A is an antigen, usually either a polypeptide (include proteins) or polysaccharide.

For the most part, benzamides will be employed in which the linking group will either be an aliphatic group or a sugar. Immunogens containing the aliphatic group will for the most part have the following formula:

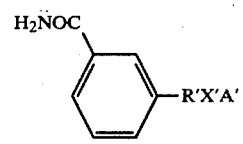

wherein:

R' is an aliphatic group of from 1to 6 carbon atoms, more usually from 2 to 5 carbon atoms having from 0 to 2 ether groups;

X' is a bond, methylene, or inorganic or organic acyl residue, particularly non-oxo-carbonyl, sulfonyl, phosphoryl, or the like; and A' is an organic antigen, particularly a polypeptide (including protein) or polysaccharide, more usually a polypeptide of at least about 2,000 molecular weight, and up to about 10 million molecular weight or higher, usually of from about 10,000 to 550,000 molecular weight, more usually of from about 40,000 to 300,000 molecular weight.

When the linking group is a sugar, the compound will for the most part having the following formula:

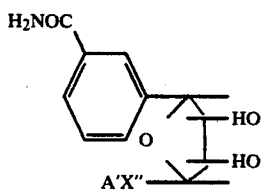

wherein: all of the symbols have been defined previously except X" which can be non-oxo-carbonyl, phosphonyl, or phosphate, usually forming an amide group with A'.

Illustrative groups defined within RX include:

TABLE I methylenecarbonyl
propylenecarbonyl
butylenecarbonyl
pentylenecarbonyl
propylenesulfonyl
ethylenephosphonyl
propylenephosphatyl
ethyleneoxyethylenecarbonyl
oxyethylenecarbonyl
oxyethylenephosphatyl
2-deoxyribouronyl
2-deoxyribo-5-phosphatyl Various antigenic compounds can be used as immunogens. Commonly employed are albumins, globulins, lipopolysaccharides, hemocyanins, enzmyes, viral proteins and the like. These compounds are conjugated with haptens in conventional ways.

Preparation of the compounds can follow conventional techniques. Preparation of the sugar derivatives can be achieved by first preparing the corresponding 5-substituted 2-(m-carboxamidophenyl) furans. These compounds may be conjugated directly to macromolecular carriers or first reduced to 2,5-dihydrofurans and the 3,4-double bond then cis-hydroxylated with osmium tetraoxide. Substitution at the meta-position can be achieved in a variety of ways, depending on the linking group and whether the linking group is joined to the annular carbon atom by carbon or oxygen. Conveniently the side chain is built into a preformed m-substituted ring. For carbon of the linking group, an aldehyde can provide a basis for extension of the linking group. For oxygen attachment to a linking group, a phenolic hydroxyl can be used. The amide may be present initially or a group may be present such as a nitrile which may be subsequently converted to the amide.

The following examples are offered by way of illustration and not by way of limitation.

EXPERIMENTAL (All temperatures are in centigrade. All parts are by weight, except for liquids which are by volume or unless otherwise indicated. The following abbreviations are used: DMSO—dimethylsulfoxide; tlc—thin layer chromatography; BSA—bovine serum albumin; NHS—N-hydroxy succinimide.)

EXAMPLE I

3(m-Cyanophenyl)acrylic acid

A mixture of 3-cyanobenzaldehyde (6.6 g, 50 mmole) malonic acid (10.4 g, 100 mmole), piperidine (2.5 ml) in 50 ml of pyridine was heated at 90°-100° under nitrogen for five hours. Complete reaction was observed on tlc (10% MeOH/CHCl$_3$, silica gel plates).

The resulting yellow solution was cooled and poured into 500 ml ice-water and the pH of the product was adjusted with 1N HCl (about 550 ml) to 2.2 using a pH meter. The white precipitate thus formed was collected by suction filtration and weighed 11.1 g. The nmr(DMSO-d$_6$) and IR(KBr) showed the correct structure.

EXAMPLE II 3-(m-Formanidophenyl)acrylic acid

The nitrile (8 g, 46 mmole) was dissolved in 50 ml of concentrated sulfuric acid at room temperature. After eighteen hours, complete reaction was observed by taking an aliquot of the reaction mixture, diluting with water and spotting on tlc (one spot Rf 0.11, 10% MeOH/CHCl$_3$ silica gel plate). The reaction mixture was then poured cautiously into ice-water (1.7 liter) and the resulting precipitate was filtered. The product, weighted 4 g after being dried in vacuo at room temperature.

EXAMPLE III

3(m-Formamidophenyl)propionic acid
(3-carboxyethylbenzamide)

A mixture of the product of Ex. II (4 g, ground into a fine powder) and platinum oxide (400 mg) suspended in a mixed solvent of 100 ml of acetone and 100 ml of methanol was hydrogenated at room temperature under 43 psi hydrogen pressure for 3 hours. The gas in the reaction vessel was then replaced with nitrogen. This procedure was repeated several times. An aliquot of the reaction mixture was spotted on tlc (20% MeOH/CHCl$_3$, silica gel plate) and showed complete reaction. The catalyst was then removed and the solvent evaporated to dryness. The resulting white precipitate was recrystallized once from water and twice from 1-propanol to yield 1.5 g of white crystals of the product mp. 184°-186°. (m/e 193, Mwt. 193), Anal. Calcd. for $C_{10}H_{11}NO_3$: C, 62.18; H, 5.70; N, 7.25. Found: C, 62.07; H, 5.92 ; N, 7.11. nmr (CF$_3$CO$_2$H) and IR (KBr) showed the correct structure.

EXAMPLE IV

Conjugate of 3-carboxyethylbenzamide to BSA

To a solution of 3-carboxyethylbenzamide (80 mg, 0.414 mmole) in 1ml of N,N-dimethylformamide (1 ml) was added to NHS (54 mg, 0.45 mmole) and 1-ethyl-3-(3-dimethylaminopropyl) carbodiimide HCl (83 mg, 0.435 mmole) under nitrogen at 5°. After 4 hours, tlc showed the formation of the N-hydroxysuccinimic ester. The NHS ester solution was then added dropwise at 5° to a solution of BSA (600 mg) in a mixture of 4 ml N,N-dimethylformamide and 10 ml tris buffer (0.05 M, pH 9) for a period of 15 minutes with constant adjustment of pH to 8.5-9 by adding 1N NaOH. The resulting reaction mixture was then stirred at 5° for 18 hours and the conjugate was passed through a Sephadex G50 column eluting with tris buffer pH8.5, and the protein fractions combined and dialyzed against water (4×4 liter) and then lyophilized to yield the 3-carboxyethylbenzamide - BSA conjugate (530 mg) with a hapten to protein ratio of 18.3 (determined by comparing the ultraviolet spectrum of the conjugate with that of a mechanical mixture of hapten and BSA).

The antisera were obtained by injecting the antigen conjugate of Ex. IV into sheep, followed by a booster injection every 2 weeks of about 0.5 mg/ml in incomplete Freund's adjuvant. One week after each booster injection, a blood sample was taken. To the serum sample (2 ml) was slowly added an equal amount of saturated ammonium sulfate at 5° to precipitate the IgG. It was then allowed to stand at 5° for 2 hrs and then centrifuged at 10K for 20 min at 4°. The supernatant was discarded and the precipitate dissolved in 0.055M tris buffer, pH 8.5, 0.05% sodium azide and 0.005% Thimerosal and the solution dialyzed with the same buffer three times.

In performing the assay, the fluorescence of NADH was measured using a Varian Fluorichrom with excitation at 340 nm and emission measured at 450 nm.

The buffer employed was 0.05M tris (pH 8.5), 0.1 mg/ml bovine gamma globulin. The NADH was dissolved in buffer and was 4 $\mu$M and the solutions were prepared freshly each day.

The assay protocol was to mix 900 $\mu$l of NADH solution and varying amounts in the range of 0 to 100 $\mu$l of antisera and sufficient assay buffer to bring the total volume to one ml. The resulting mixture was incubated at room temperature for 1.5 hr. The same procedure was employed for determining the fluorescence background of the antiserum except that in place of the NADH solution was substituted buffer solution having no NADH. The antiserum employed was from the second bleed. The following table indicates the results. The fluorescence readings are reported as the fluoroescence observed with the NADH solution in the presence of varying amounts of antiserum reduced by the fluorescence of the antiserum in the absence of NADH, the fluoresence observed in the presence of non-specific antersium reduced by the fluorescence of the non-specific antiserum in the absence of NADH, and the enhancement observed due to the binding of the NADH to the antiserum.

TABLE II

| Run | $\mu$l immunoglobulin added | Fluorescence reading* antiNADH | IgG | Difference |
|---|---|---|---|---|
| 1 | 0 | 323 | 323 | 0 |
| 2 | 10 | 301 | 278 | 23 |
| 3 | 20 | 310 | 259 | 51 |
| 4 | 50 | 344 | 247 | 97 |
| 5 | 75 | 380 | 230 | 150 |
| 6 | 100 | 427 | 236 | 191 |

*The IgG is gamma globulin to provide a control to subtract out non-specific effects.

In order to assay for NADH, varying amounts of 10 $\mu$M NADH solution were mixed with 200 $\mu$l of antiserum and 2.0 ml of buffer and read substantially immediately. The antiserum was from the fourth bleed. Table III shows the fluorescence signal observed with 200 $\mu$l of antiserum, with 200$\mu$l of buffer used in the place of antiserum, and the fluorescence enhancement due to the binding of the NADH to the antiserum.

TABLE III

| Run | NADH, $\mu$l | Fluorescence reading antiNADH | Buffer | Difference |
|---|---|---|---|---|
| 7 | 0 | 0 | 0 | 0 |
| 8 | 20 | 12 | 1.5 | 10.5 |
| 9 | 40 | 21 | 3 | 18 |
| 10 | 50 | 24 | 4 | 20 |
| 11 | 100 | 31 | 7 | 24 |
| 12 | 150 | 41 | 11 | 30 |

Table IV shows the results of a similar experiment in which 200 $\mu$l of the buffer was replaced by 200$\mu$ of 1mM NAD.

TABLE IV

| Run | NADH, $\mu$l | Fluorescence reading antiNADH + NAD | Buffer + NAD | Difference |
|---|---|---|---|---|
| 14 | 0 | 0 | 0 | 0 |
| 14 | 20 | 4.5 | 0.5 | 4 |
| 15 | 50 | 9 | 1.5 | 7.5 |
| 16 | 100 | 15 | 2.5 | 12.5 |
| 17 | 150 | 20 | 4.5 | 15.5 |
| 18 | 200 | 22 | 6.5 | 15.5 |
| 19 | 250 | 26 | 8 | 18 |

It is evident from the above results that substantial enhancement is observed by combining the antisera prepared in the subject invention with NADH in the presence or absence of large amounts of NAD. The fluoresecent signal observed with NADH can therefore be enhanced without interference from the varying components normally included in a wide variety of enzyme assays and competitive protein binding assays. Thus, greater sensitivity can be achieved, lower amounts or concentrations of reagents can be employed, faster assays can be performed, or combinations thereof. Furthermore, it is particularly significant that, in accordance with the subject invention, antisera can be obtained that distinguishes NADH from NAD, with the immunogen employed as a conjugate of a compound which simulates the reduced form of nicotinamide.

Although the foregoing invention has been described in some detail by way of illustration and example for purposes of clarity of understanding, it will be obvious that certain changes and modifications may be practiced within the scope of the appended claims.

We claim:

1. In an assay employing the transformation from the oxidized to the reduced form of a coenzyme having an N-substituted pyridyl prosthetic group by measuring the change in fluorescence of said assay medium as related to the amount of analyte in said assay medium, wherein analyte is combined with receptor for said analyte and an enzyme label is employed requiring said co-enzyme and the amount of co-enzyme formed is related to the amount of analyte in said assay medium, and after combining said analyte and antisera in the presence of said label, said fluoresence is measured, the improvement which comprises adding antisera capable of cross reacting with meta-substituted benzamide and the reduced form of the coenzyme and capable of binding to the reduced form of the coenzyme in the presence of the oxidized form to enhance the measurement of fluorescence.

2. A method according to claim 1, wherein said analyte is an enzyme.

3. A method according to claim 2, wherein said enzyme is a NAD dependent dehydrogenase.

4. A method according to claim 3, wherein said analyte is a ligand, wherein the rate of transformation to the reduced form by an enzyme is related to the amount of ligand present in said assay medium.

5. A method according to claim 4, wherein said enzyme is an enzyme-ligand conjugate.

6. A method according to any of claims 1-4 or 5 wherein said antibodies are conjugated with an energy transfer compound capable of transferring energy equivalent to light of a wavelength in the range of about 320 to 400 nm.

* * * * *